United States Patent [19]
Jannetta

[11] Patent Number: 5,589,183
[45] Date of Patent: Dec. 31, 1996

[54] METHOD AND APPARATUS FOR TREATMENT OF NEUROGENIC DIABETES MELLITUS, AND OTHER CONDITIONS

[76] Inventor: Peter J. Jannetta, 214 Schenley Rd., Pittsburgh, Pa. 15217

[21] Appl. No.: 539,341

[22] Filed: Oct. 5, 1995

[51] Int. Cl.$^6$ ....................................................... A61F 2/02
[52] U.S. Cl. ................................................................ 424/423
[58] Field of Search ............................................ 424/423

[56] References Cited

PUBLICATIONS

From the Surgical Clinic at Johns Hopkins Hospital and University, "Section of the Sensory Root of the Trigeminal Nerve at the Pons, Preliminary Report of the Operative Procedure", Walter E. Dandy, undated, pp. 105–106.

"The Treatment of Trigeminal Neuralgia by the Cerebellar Route", Walter E. Dandy, M.D., undated, pp. 787–795.

"Treatment of Meniere's Disease by Section of Only the Vestibular Portion of the Acoustic Nerve", by Walter E. Dandy, M.D., Jun. 2, 1933, pp. 52–55.

"The Arterial Relations of the Internal Auditory Meatus", by Sydney Sunderland, 1945, pp. 23–27.

Department of Neurological Surgery, The Cleveland Clinic Foundation, Cleveland, Ohio, "Concerning the Mechanism of Trigeminal Neuralgia and Hemifacial Spasm", W. James Gardner, M.D., May 31, 1962, pp. 947–958.

*Neuro–Chirurgie*, Tome 16, No. 6, "Travaux Originaux Microchirurgie du trijumeau:Anatomie fonctionnelle", by J. Provost and J. Hardy, Nov., 1970, pp. 459–470.

*The Western Journal of Medicine*, "Microsurgical Treatment of Hemifacial Spasm", by H. L. Hankison, M.D. and Charles B. Wilson, M.D., Mar., 1976, pp. 191–193.

*Inst. Neurol Madras, Proc.*, –vol. 6, "Arterial Compression of the Trigeminal Nerve at the Pons as a Cause of Trigeminal Neuralgia", by P. G. Petty, Feb., 1976, pp. 93–95.

*Neurosurgery*, vol. 1, No. 1, "A Comparison of Percutaneous Radiofrequency Trigeminal Neurolysis and Microvascular Decompression of the Trigeminal Nerve for the Treatment of Tic Douloureux",: by Ronald I. Apfelbaum, M.D., Congress of Neurological Surgeons, 1977, pp. 16–21.

*Jama*, "Management of Tic Douloureux", vol. 240, No. 16, Oct. 13, 1978, p. 1715.

*Acta Neurochirurgica*, vol. 59, "Treatment of Neurogenic Torticollis by Microvascular Lysis of the Accessory Nerve Roots–Indication, Technique and First Results", by N. Freckmann, R. Hagenah, H.–D. Hermann, and D. Muller, 1981, pp. 167–175.

(List continued on next page.)

*Primary Examiner*—Carlos Azpuru
*Attorney, Agent, or Firm*—Buchanan Ingersoll, P.C.; Michael L. Dever

[57] ABSTRACT

A method and implants provide for relieving pressure from a region of the brainstem within the cranium of a subject with a neuroendocrine servomechanism. The pressure results from the compression of the region by a blood vessel. The method includes gaining access to the region using a first surgical technique; exposing the region according to a second surgical technique; lifting the blood vessel from the region according to a third surgical technique, thereby providing the pressure relief; and inserting a neurovascular bridge implant between the blood vessel and the region to maintain the pressure relief. The neuroendocrine servomechanism is responsive to the pressure relief on the region, causing amelioration of a disease. One neuroendocrine servomechanism can include the pancreas of the subject, and the pressure relief ameliorates non-insulin-dependent diabetes mellitus. The neurovascular bridge implant can be a preconfigured shredded plastic implant, made of polytetrafluoroethylene, or a preconfigured thermoplastic implant, made of a polyurethane-based material having a glass-transition temperature of between 20° C. to 60° C. and a transition band of about 8° C.

25 Claims, 7 Drawing Sheets

PUBLICATIONS

*Neurosurgery,* vol. 14, No. 3, "Microvascular Decompression of the Eighth Cranial Nerve for Disabling Tinnitus without Vertigo: A Case Report", Tadashi Kudo, M.D., D.M.Sc. and Kenjiro Ito, M.D., D.M.Sc., 1984 by the Congress of Neurological Surgeons, pp. 338–340.

*J. Neurosurg.,* vol. 62, "Hemiparesis caused by vertebral artery compression of the medulla oblongata", Phyo Kim, M.D. et al., Mar., 1985, pp. 425–429.

*Arch Neurol.* vol. 43, "Surgical Decompression of the Facial Nerve in the Treatment of Chronic Cluster Headache", Seymour Solomon, M.D., Ronald L. Apfelbaum, M.D., May, 1986, pp. 479–482.

*Advances in Neurosurgery,* vol. 17, "Neurovascular Compression as a Cause of Essential Hypertension: A Microanatomical Study", R. Naraghi, M. R. Gaab and G. F. Walter, 1989, pp. 182–186.

*Diagnostic Neurotology,* "Vascular Compression Syndrome of the Eighth Nerve" Clinical Correlations and Surgical Findings, Margareta B. Moller, M.D. and Aage R. Moller, Ph.D, Neurologic Clinics, vol. 8, No. 2, May, 1990, pp. 421–439.

Reprinted from *Annals of Otology, Rhinology & Laryngology,* "Results of Microvascular Decompression of the Eighth Nerve as Treatment for a Disabling Positional Vertigo", Margareta B. Moller, M.D., Sep., 1990, vol. 99, No. 9, pp. 724–729.

*J. Neurosurg.,* vol. 76, "Neurovascular compression in trigeminal neuralgia: a clinical and anatomical study", Peter J. Hamlyn, M.B., B.S., F.R.C.S., and Thomas T. King, F.R.C.S., Jun., 1992, pp. 948–954.

*J. Neurosurg.* vol. 79, "Neurogenic hypertension related to basilar impression", Lawrence D. Dickinson, M.D., et al., Dec., 1993, pp. 924–928.

Reprinted from *Current Topics in Surgical Research,* vol. 2, "Microsurgical Exploration and Decompression of the Facial Nerve in Hemifacial Spasm", Peter J. Jannetta, M.D., 1970, Academic Press, Inc., New York, pp. 217–220.

Reprinted from *Surgical Forum,* vol. XXI, "Electromyographic and Electron Microscopic Correlates in Hemifacial Spasm Treated by Microsurgical Relief of Neurovascular Compression", Peter J. Jannetta, M.D., et al. 1970.

*Clin. Neurosurg.,* Chapter 40, vol. 24, "Treatment of Trigeminal Neuralgia by Suboccipital and Transtentorial Cranial Operations", Peter J. Jannetta, M.D., 1977, pp. 538–549.

*J. Neurosurg.,* vol. 47, "Etilogy and definitive microsurgical treatment of hemifacial spasm", Peter J. Jannetta, M.D., et al., Sep., 1977, pp. 321–328.

*J. Neurosurg.,* vol. 47, "Glossopharyngeal neuralgia", Ranjit K. Laha, M.D. and Peter J. Jannetta, M.D., Sep., 1977, pp. 316–320.

*Neurochiurgia Advances Fortschritte,* vol. 20, "Observations on the Etiology of Trigeminal Neuralgia, Hemifacial Spasm, Acoustic Nerve Dysfunction and Glosspharyngeal Neuralgia, Definitive Microsurgical Treatment and Results in 117 Patients". Peter J. Jannetta, M.D., Sep., 1977, pp. 145–154.

Reprint from *The Laryngoscope,* vol. LXXXVIII, No. 5, "Bell's Palsy: A Theory as to Etiology, Observations in Six Patients," Peter J. Jannetta, M.D., and David J. Bissonette, B.A., B.S., S.A., May, 1978, pp. 849–854.

*J. Neurogsur,* vol. 50, "Arterial cross compression of the trigeminal nerve at the pons in trigeminal neuralgia", Stephen J. Haines, M.D., et al., Feb., 1979, pp. 257–259.

Reprinted from *Clinical Neurosurgery,* Chapter 26, "Microsurgery of Cranial Nerve Cross-Compression", Peter J. Jannetta, M.D., 1979, pp. 607–615.

*Journal of Computer Assisted Tomography,* vol. 3, No. 6, "Tortuous Vertebrobasilar Arteries Causing Cranial Nerve Syndromes: Screening by Computed Tomography", Ziad L. Deeb, et al., 1979, pp. 774–778.

Reprint from *Surgial Forum,* vol. XXX, "Clinical Observations on Etiology of Essential Hypertension", Peter J. Jannetta, M.D., FACS, and Howard M. Gendell, M.D., 1979, 431–432.

Reprint from *Surgical Forum,* vol. XXX, "Cardiovascular Response to Pulsatile Pressure Applied to Ventrolateral Medulla", Ricardo Segal, et al., 1979, pp. 433–435.

*J. Neurosurg.,* vol. 52, "Microvascular relations of the trigeminal nerve An anatomical study with clinical correlation", Stephen J. Haines, M.D., et al., Mar., 1980, pp. 381–386.

*Neurosurgery,* vol. 6, No. 3, "Neurinoma of the Trigeminal Root and Atypical Trigeminal Neuralgia: Their Commonality", Howard Yonas, M.D. and Peter J. Jannetta, M.D., 1980, pp. 273–277.

*Neurosurgery,* vol. 7, No. 4, "Trigeminal Neuropathy–New Observations", Peter J. Jannetta, M.D., and Lynn J. Robbins, M.D., 1980, pp. 347–351.

Reprinted from *Annals of Surgery,* vol. 192, No. 4, "Neurovascular Compression in Cranial Nerve and Systemic Disease", Peter J. Jannetta, M.D., 1980, pp. 518–525.

*Electroencephalograpy and Clinical Neurophysiology,* "Intracranially Recorded Responses From the Human Auditory Nerve: New Insights into the Origin of Brain Stem Evoked Potentials (BSEPs).", Aage R. Moller, et al., 1981, pp. 18–27.

From the Divisions of Physiological Acoustics, Audiology and Speech Pathology, "Neural Generators of Brainstem Evoked Potentials Results from Human Intracranial Recordings", Aage R. Moller, Ph.D., et al., Presented at Meeting of the American Otological Society, Inc., Vancouver, British Columbia, May 9–10, 1981, pp. 591–596.

*Clin. Neurosurg.,* Chapter 25, "Cranial Nerve Vascular Compression Syndromes (Other than Tic Douloureux and Hemifacial Spasm)", Peter J. Jannetta, M.D., 1981, pp. 445–456.

Reprinted from *Angiology,* vol. 33, No. 3, "Hemodynamic Changes Induced by Pulsatile Compression of the Ventrolateral Medulla", Ricardo Segal, M.D., et al., Mar., 1982, pp. 161–172.

*Arch Otolaryngol,* vol. 108, "Intracranially Recorded Auditory Nerve Response in Man New Interpretations of BSER", Aage R. Moller, Ph.D., et al., Feb., 1982, pp. 77–82.

*Electroencephalography and Clinical Neurophysiology,* "Evoked Potentials From the Inferior Colliculus in Man", Aage R. Moller and Peter J. Jannetta, 1982, pp. 612–620, vol. 53.

*J. Neurosurg.,* vol. 57, "Implanted pulsatile balloon device for simulation of neurovascular compression syndromes in animals", Richard Segal, M.D., et al., Nov., 1982, pp. 646–650.

*Neurosurgery,* vol. 13, No. 3, "Evoked Potentials in Trigeminal Neuralgia", M. H. Bennett, Ph.D. and P. J. Jannetta, M.D., 1983, pp. 242–247.

*Neurosurgery,* vol. 14, No. 1, "Hemifacial Spasm Caused by a Venule: Case Report", Peter J. Jannetta, M.D., 1984, pp. 89–92.

Reprint from *The New England Journal of Medicine*, "310, Disabling Positional Vertigo", Peter J. Jannetta, et al., Jun. 28, 1984, pp. 1700–1705.

Reprint from *Neurology*, vol. 34, No. 7, "Pathophysiology of hemifacial spasm: III. Effects of facial nerve decompression", Viggo Kamp Nielsen, M.D., Ph.D., and Peter James Jannetta, M.D., pp. 891–897, Jul., 1984.

*J. Neurosurg.*, vol. 61, "On the origin of synkinesis in hemifacial spasm: results of intracranial recordings", Aage R. Moller, Ph.D., and Peter J. Jannetta, M.D., Sep., 1984, pp. 569–576.

*J. Neurosurg*, vol. 61, "Tic convulsif: results in 11 cases treated with microvascular decompression of the fifth and seventh cranial nerves", Bruce R. Cook, M.D., and Peter J. Jannetta, M.D., Nov., 1984, pp. 949–951.

*Ann. Surg.*, "Neurogenic Hypertension: Etiology and Surgical Treatment, I. Observations in 53 Patients", Peter J. Janetta et al., Oct., 1984, pp. 391–398.

Reprint from *Neurology*, vol. 35, No. 5, "Vascular compression, hemifacial spasm, and multiple cranial neuropathy", Benjamin H. Eidelman, M.D., Ph.D., et al., May, 1985, pp. 712–716.

Reprint from *Annals of Surgery*, vol. 202, No. 2, "Neurogenic Hypertension: Etiology and Surgical Treatment, II. Observations in an Experimental Nonhuman Primate Model", Peter J. Jannetta et al., Aug., 1985, pp. 253–261.

Reprint from *Neurology*, vol. 35, No. 7, "Hemifacial spasm: Results of electrophysiologic recording during microvascular decompression operations", Aage R. Moller, PhD, and Peter J. Jannetta, M.D., Jul., 1985, pp. 969–974.

*J. Neurosurg*, vol. 64, "Diagosis and surgical treatment of disabling positional vertigo", Margareta B. Moller, M.D., Ph.D., et al., Jan., 1986, pp. 21–28.

Reprint from *Clinical Neurosurgery*, vol. 33, "Neurosurgical Treatment of Vertigo by Microvascular Decompression of the Eighth Cranial Nerve",: Peter J. Jannetta, et al., 1986, pp. 645–665.

*Neurosurgery*, vol. 20, No. 5, "Hemifacial Spasm in Young People Treated with Microvascular Decompression of the Facial Nerve", Hae Dong Jho, M.D., Ph.D., and Peter J. Jannetta, M.D., 1987, pp. 767–770.

*J. Neurosurg.*, vol. 68, Apr., 1988, "Bilateral trigeminal neuralgia: a 14–year experience with microvascular decompression", Ian F. Pollack, M.D., et al., Apr., 1988, pp. 559–565.

Case Report of the *Journal of Craniomandibular Disorders: Facial & Oral Pain*, vol. 5, No. 3, "Trigeminal Neuralgia and Its Treatment in a 13–Month–Old Child: A Review and Case Report", William E. Mason, DDS, M.S. et al., 1991, pp. 213–216.

Reprint from *Laryngoscope*, vol. 103, No. 4, "Vascular Decompression Surgery for Severe Tinnitus: Selection Criteria and Results", Margareta B. Moller, M.D., DMSc., et al., Apr., 1993, pp. 421–427.

*The American Journal of Otology*, vol. 14, No. 4, "Restoration of Useful Hearing After Microvascular Decompression of the Cochlear Nerve", Gail L. Rosseau, M.D., et al., Jul., 1993, pp. 392–397.

*Acta Neurochirurgica*, No. 125, "Microvascular Decompression of the Eighth Nerve in Patients with Disabling Positional Vertigo: Selection Criteria and Operative Results in 207 Patients", M. B. Moller, et al., 1993, pp. 75–82.

*J. Neurosurg.*, vol. 81, "Microvascular decompression for trigeminal neuralgia caused by vertebrobasilar compression", Mark E. Linskey, M.D., et al., Jul., 1994, pp. 1–9.

*Neurosurgery*, vol. 36, No. 1, "Microvascular Decompression for Glossopharyngeal Neuralgia", Daniel K. Resnick, M.D., et al., Jan., 1995, pp. 64–69.

*J. Neurosurg.*, vol. 82, "Microvascular decompression for hemifacial spasm", Fred G. Barker, II, M.D., et al., Feb., 1995, pp. 201–210.

*Acta Neurochirurgica*, No. 134, "Microvascular Decompression for Spasmodic Torticollis", H. D. Jho and P. J. Jannetta, 1995, pp. 21–26.

*Prog. neurol. Surg.*, vol. 7, "Microsurgical Approach to the Trigeminal Nerve for Tic Douloureux", Peter J. Jannetta, 1976, pp. 180–200.

A Reprint from *Operative Surgery*. Third Edition, "Hemifacial Spasm: Microvascular Decompression of the V11th Nerve Intracranially", Peter J. Jannetta, undated, pp. 374–381, 1978.

*Neurosurgery*, Section D, "Neurovascular Compression Syndromes 238 Posterior Fossa Neurovascular Compression Syndromes Other Than Neuralgias", Peter J. Jannetta, 1984, pp. 1901–1906.

Chaper 26, "Microvascular Decompression for Hemifacial Spasm", Peter J. Jannetta, undated, pp. 499–508.

*Neurosurgical Procedures: Personal Approaches to Classic Operations*, "Microvascular Decompression of the Facial Nerve for Hemifacial Spasm", Peter J. Jannetta, M.D., 1992, pp. 154–162.

*Neurological Surgery*, vol. 3, No. 1, "Essential Hypertension Caused by Arterial Compression of the Left Lateral Medulla: A Follow–Up", Peter J. Jannetta et al., 1992, pp. 107–125.

European Foundation of E.U.F.O.S., *Volumetto Estratto DA:*, "The new frontiers of Oto–Rhino–Laryngology in Europe", 'Results of microvascular decompression ('MVD') surgery in patients with disabling positional vertigo (DPV),' M. B. Moller, et al., 1992, 429–432.

*Surg. Neurol.*, vol. 4, "Hemifacial Spasm: Ultrastructural Changes in the Facial Nerve Induced by Neurovascular Compression", John R. Ruby, M.D., and Peter J. Jannetta, Oct., 1975, pp. 369–370.

"Arterial Compression of the Trigeminal Nerve at the Pons in Patients with Trigeminal Neuralgia", Peter J. Jannetta, pp. 159–162.

"Gross (Mesoscopic) Description of the Human Trigeminal Nerve and Ganglion", Peter J. Jannetta, M.D., pp. 109–111.

*"Working in a very small place—The making of a neurosurgeon"*, Mark Shelton, Vintage Books, 1989.

*J. Neurosurg.* vol. 65, Letter to the Editor and references, Nov., 1986, pp. 725–727 and *J. Neurosurg.*, vol. 66, Letter to the Editor and references, Apr., 1987, p. 635.

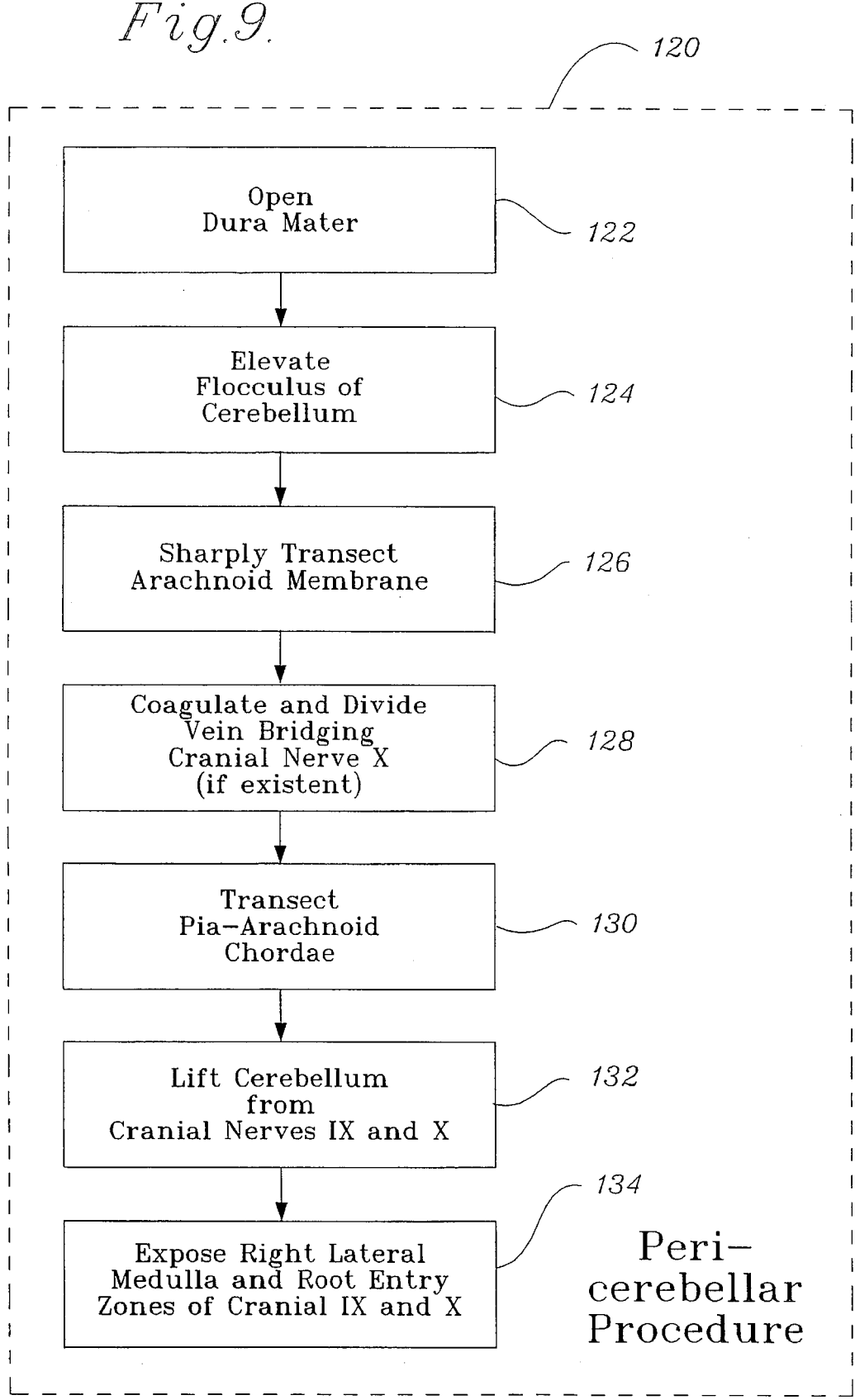

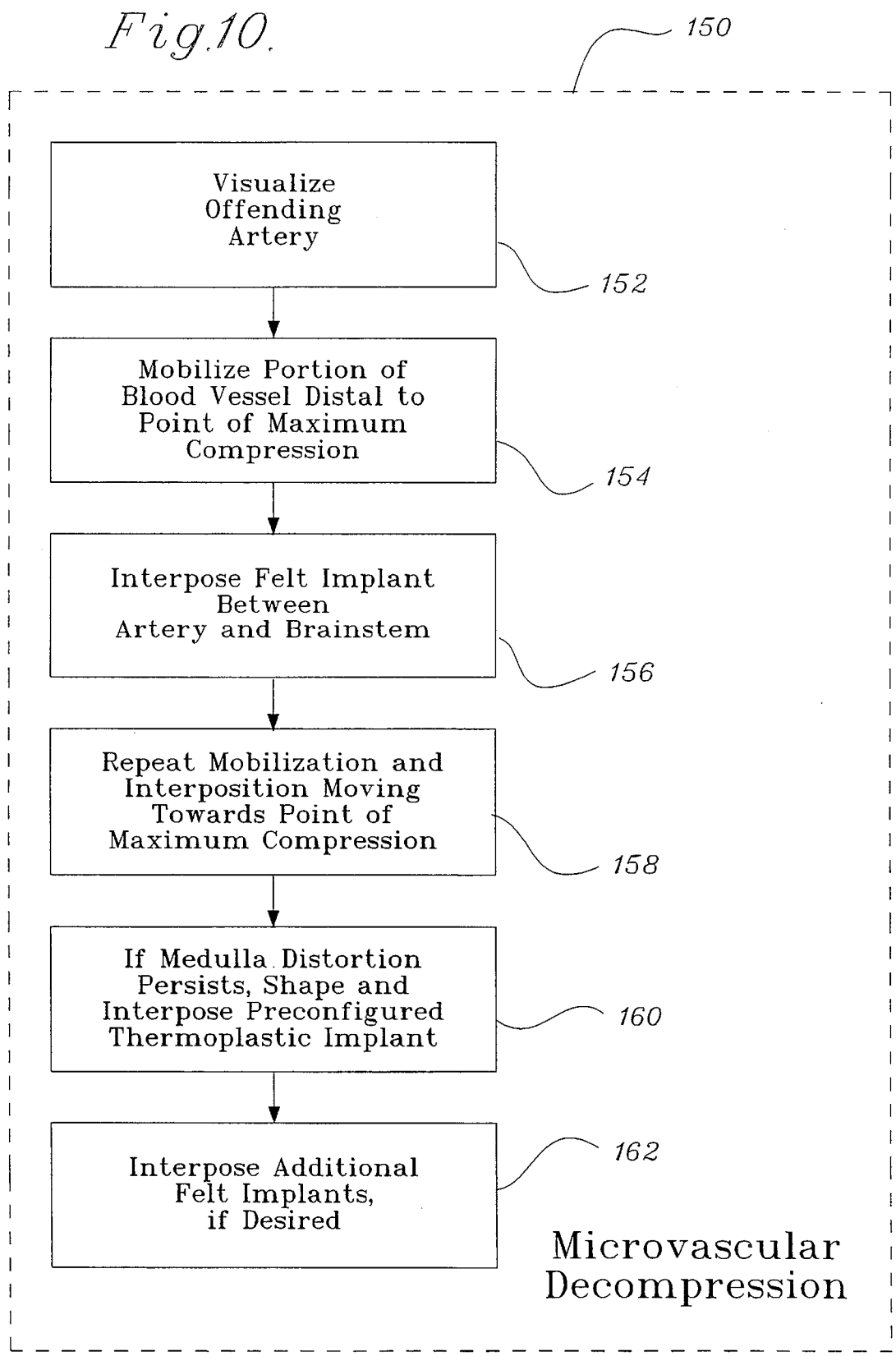

METHOD AND APPARATUS FOR TREATMENT OF NEUROGENIC DIABETES MELLITUS, AND OTHER CONDITIONS

BACKGROUND OF THE INVENTION

1. Field of the Invention

This invention relates to the field of neurosurgery, in particularly, a neurosurgical treatment for neurogenic disorders and, more specifically, to a neurosurgical method for the treatment of neurogenic conditions, including diabetes mellitus, by microvascular decompression of the medulla oblongata and viscera-related cranial nerves.

2. Background Art

Prior to the advance of microsurgical techniques, many intracranial procedures in the area of the brainstem were considered too risky and were not performed. With the introduction of the surgical microscope into neurosurgical practice, the intracranial vasculature and nearby neural structures could be visualized, thus facilitating the identification of subtle defects such as microvascular compression of the brainstem. Using microsurgical techniques, specific portions of the brain stem, cranial nerves, and minute blood vessels adjacent thereto can be manipulated to repair these defects.

One such microsurgical technique is microvascular decompression (MVD). In MVD, the surgeon typically identifies the locus of vascular compression, elevates the offending blood vessel or vessels from the surface of the affected neural tissue, and interposes a soft, biocompatible implant between the blood vessel and the neural tissue to maintain the decompression.

In general, as humans age, blood vessels tend to enlarge and may become ectatic, tortuous, and in many cases, sclerotic. To a large extent, the characteristics of a subject's vasculature are inherited and, therefore, heredity is considered to be a major factor in cerebrovascular pathophysiology. As certain subjects age, the intracranial blood vessels which surround the medulla oblongata such as the basilar and verterbal arteries, can press into the surface of the medulla. This compression can produce grooving of the medullary surface, which can alter the function of the anatomical entities innervated by the affected region of the medulla. Where arteries impinge upon the medulla and the cranial nerves, a pulsatile compression of those neural tissues is produced.

Vascular compression of certain cranial nerves has been found to create, or contribute to, numerous diseases or conditions, including for example, trigeminal neuralgia, audiovestibular dysfunction and hemifacial spasm, and glossopharyngeal neuralgia. For example, Jannetta discusses the etiologies, and treatments for, the aforementioned diseases in "Microsurgery of Cranial Nerve Cross-Compression," CLINICAL NEUROSURGERY, Chap. 26, pp. 607–15 (1979). Each disease can be considered a hyperactive dysfunction of the respective cranial nerves V, VII, VIII, IX, and X, most likely due to root entry zone abnormalities that are usually vascular in nature. There is evidence that brainstem compression, and vascular cross-compression at the root entry zone of cranial nerves, are related to a number of clinical syndromes. Microvascular decompression can be an extremely effective treatment for each of these diseases, with nerve function becoming greatly improved, if not fully normal, as a result.

Furthermore, pulsatile compression of the left lateral medulla oblongata by looping cerebral arteries at the base of the brain has been shown to cause neurogenic or "essential" hypertension. Jannetta, et al., describes the treatment of neurogenic hypertension using microvascular decompression of the left lateral medulla in "Essential Hypertension Caused by Arterial Compression of the Left Lateral Medulla: A Follow-Up," *Perspec. Neurol. Surg.*, 3 (1): 107–125 (1992).

It is believed that other diseases, including non-insulin-dependent diabetes mellitus (NIDDM), also may be caused or exacerbated by compressive cerebrovascular pathophysiology, particularly pulsatile vascular compression of the right lateral medulla. In general, diabetes mellitus is a syndrome resulting from a variable interaction of hereditary and environmental factors It is characterized by abnormal insulin secretion, inappropriately elevated blood glucose levels, and a variety of end organ complications including nephropathy, retinopathy, neuropathy, and accelerated atherosclerosis. Patients with NIDDM may or may not use insulin for symptom control, but do not need it for survival. In NIDDM, tissue processes which control carbohydrate metabolism are believed to develop a decreased sensitivity to insulin over time. The progression of NIDDM is associated with increasing concentrations of blood glucose, and is coupled with a relative decrease in the rate of glucose-induced insulin secretion.

There is evidence that a relative excess of insulin, or hyperinsulinemia, may be associated with accelerated atherosclerosis, hypertension, hypertriglyceridemia, and reduced high-density lipoprotein cholesterol. Because insulin also is capable of causing insulin resistance, hyperglycemia can co-exist with hyperinsulinemia in patients with early NIDDM. Treatment of NIDDM typically includes weight control, regulation of diet, and the administration of either oral hypoglycemic agents or insulin. Such solutions are not entirely satisfactory because NIDDM patients acquire the sequelae typically associated with both hyperinsulinemia, e.g., accelerated atherosclerosis, hypertension, etc., and hyperglycemia, e.g., microvascular complications including nephropathy, retinopathy, neuropathy, etc. In general, it was thought although the progression of NIDDM could be slowed, but the ultimate effects of the disease were inexorable.

Although the cause of NIDDM is not fully understood, it is believed to be strongly influenced by hereditary factors due to its prevalence in particular families. Unlike insulin-dependent diabetes mellitus, which is thought to be caused by the autoimmune destruction of the insulin-producing cells of the pancreas, NIDDM is believed to be, at least at its inception, a decline and eventual failure of the neural and hormonal servomechanisms that promote euglycemia. Indeed, in early NIDDM, hyperglycemia and hypertension are epiphenomena.

Also, NIDDM is strongly associated with "apple" obesity, in which the subject develops a large abdomen with normal-sized limbs and lower torso. Heredity, too, plays a significant role in the incidence of "apple" obesity, in which the omentum enlarges, and which may be due to a breakdown in the fat storage servomechanism involving the abdominal adipose tissue and the omentum. Because insulin acts as a "fat-sparing" substance, the increased insulin levels of NIDDM also tend to promote obesity. A common link may exist between NIDDM and "apple" obesity because both appear to be products of a disruption of the internal milieu for glucose and fat servomechanisms and both the pancreas and omentum are innervated by fibers from cranial nerve X, the vagus nerve.

To the extent that the aforementioned servomechanisms promoting euglycemia can be restored prior to the exhaustion of the pancreas and the development of atherosclerosis and microvascular complications, NIDDM may be cured, or its effects be greatly ameliorated. At present, however, there is no commonly-accepted surgical procedure in use for the treatment of non-insulin-dependent diabetes mellitus.

What is needed then is a method and devices for treating a neuroendocrine disease, such as NIDDM, that is caused or exacerbated by microvascular compression of the brainstem tissue and associated cranial nerves.

SUMMARY OF THE INVENTION

The invention described herein provides a method and devices for relieving pressure from a preselected region of the brainstem within the cranium of a subject, where the subject has a neuroendocrine servomechanism, and the pressure results from the compression of the region by a blood vessel. In general, the method includes gaining access to the preselected region using a first preselected surgical technique; exposing the preselected region according to a second preselected surgical technique; lifting the blood vessel from at least a portion of the region according to a third preselected surgical technique, thereby providing the pressure relief; and inserting a neurovascular bridge implant between the blood vessel and the preselected region, the implant maintaining the pressure relief. Typically, the neuroendocrine servomechanism is responsive to the pressure relief on the region, causing amelioration of a disease. In one embodiment of the method according to the invention herein, the neuroendocrine servomechanism includes the pancreas of the subject, and the pressure relief ameliorates non-insulin-dependent diabetes mellitus.

In one embodiment of the method, the first preselected surgical technique can be a retromastoid craniectomy; the second preselected surgical technique can be a pericerebellar procedure; and the third preselected surgical technique can be microvascular decompression. The preselected region can include a portion of medulla oblongata, such as the right ventrolateral medulla oblongata, or tenth cranial nerve, or both. The blood vessel typically is an artery such as the basilar artery, the vertebral artery, the anterior inferior cerebellar artery, or the posterior inferior cerebellar artery, and branches and combinations thereof, which causes pulsatile compression of the preselected region.

The neurovascular bridge implant according to the invention herein can be a preconfigured shredded plastic implant, or a preconfigured thermoplastic implant. The preconfigured shredded plastic implant can be made of polytetrafluoroethylene. The preconfigured thermoplastic implant has a shape-memory function, and can be made of a polyurethane-based material having a glass-transition temperature of between about 20° C. and about 60° C. and a transition band of about 8° C.

BRIEF DESCRIPTION OF THE DRAWINGS

FIG. 9 is a flow diagram of one embodiment of a pericerebellar procedure according to the invention herein.

FIG. 10 is a flow diagram of one embodiment of a microvascular decompression procedure according to the invention herein.

DESCRIPTION OF THE INVENTION

The invention herein provides a method and devices for treating a neuroendocrine disease that is caused or exacerbated by vascular compression of the brainstem and the associated cranial nerves. By initiating and maintaining decompression of the relevant neural tissue, the diminished neuroendocrine servomechanisms can be encouraged to regain sufficient functioning as to effect the elimination or long term amelioration of the target neuroendocrine disease, e.g., NIDDM.

In one embodiment of the present invention, it is preferred to treat NIDDM by effecting microvascular decompression of the right ventrolateral medulla oblongata, and the associated ninth and tenth cranial nerves (Cranial IX and Cranial X, respectively) using microsurgical techniques. Access to a subject's medulla and cranial nerves can be obtained by performing, for example, a retromastoid craniectomy, followed by a pericerebellar procedure which includes transection of the meninges and traversal of the cerebellum to the medulla oblongata. With the vertebral-basilar arteries thus visualized, the surgeon can perform a microvascular decompression of those pulsatile vessels which are compressing, or even grooving, the surfaces of the medulla and cranial nerves.

Figure 1:
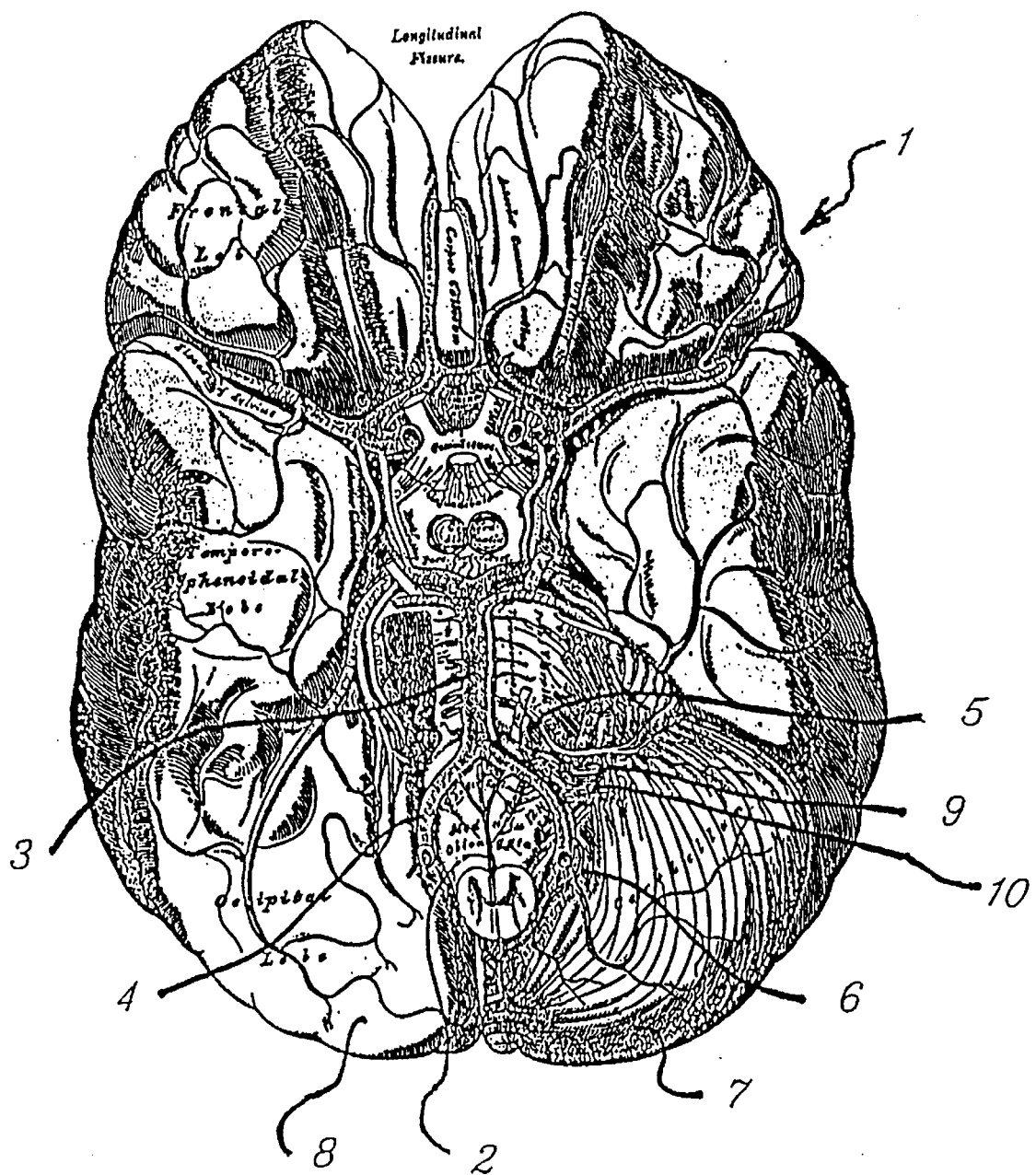
FIG. 1 is a basilar view of the brain illustrating the blood vessels and cranial nerves at the base of the brain.

FIG. 1 is a basilar view of a brain 1 showing parallel views of the blood vessels at the base of the brain and the cranial nerves. Visible from this view are medulla oblongata 2, basilar artery 3, and the bifurcated vertebral artery 4. A relevant branch of basilar artery 3 is anterior inferior cerebellar artery (AICA) 5, and of vertebral artery 4 is posterior inferior cerebellar artery (PICA) 6. The left portion of cerebellum 7 is shown, and the right portion is removed to show occipital lobe 8. Other visible neural structures include Cranial IX, nerve 9 and Cranial X, nerve 10. FIG. 1 shows that arteries 3–6, and their branches, are quite proximate to, if not in contact with, medulla oblongata 2. As an individual ages, and as heredity dictates, all arteries in the brain, including arteries 3–6, tend to enlarge. In some cases, such as with neurogenic NIDDM, arteries 3–6, alone or in combination, can compress the surface of the medulla oblongata 2, near the root entry of nerves 9 and 10, and may cause grooving of the medullary tissue. Because of the pulsatile nature of the blood flow through arteries 3–6, the compression tends to be pulsatile compression. It is believed that pulsatile compression of the right ventrolateral medulla oblongata 2 causes the degradation of the glucose regulatory mechanism that acts in concert with the subject's internal milieu.

Figure 2:
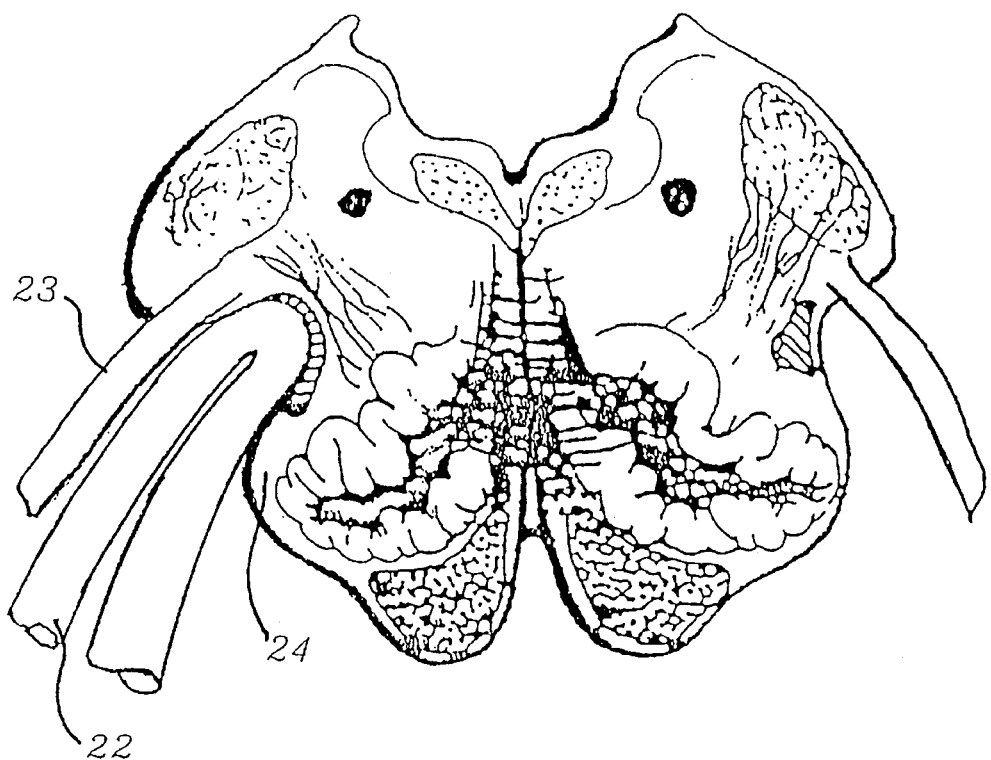
FIG. 2 is a top view of a cross-section of a normal medulla oblongata at the root entry zone of the cranial nerve X.

FIG. 2 is the top view of a cross-section of medulla oblongata 20 that is compressed by vertebral artery loop 22 near the root entry zone of the right branch 23 of Cranial X. Branch 23 provides the fibers of the vagus nerve which innervate the abdominal viscera, including the pancreas and the omentum. The compression of region 24 by pulsatile loop 22 can disrupt normal neuroendocrine activities and lead to aberrant glucose and insulin regulation. As the course of NIDDM progresses, loop 22 can enlarge further and become sclerotic, producing even greater compression of region 24. Eventually, such prolonged, progressive compression of region 24 can severely diminish, if not extinguish, the neuroendocrine activities of region 24, and NIDDM can become advanced and, perhaps, irreversible. However, by microvascular decompression of region 24, early in the development of NIDDM, glucose and insulin neuroendocrine dysfunction can be substantially improved, if not completely reversed.

Figure 3:
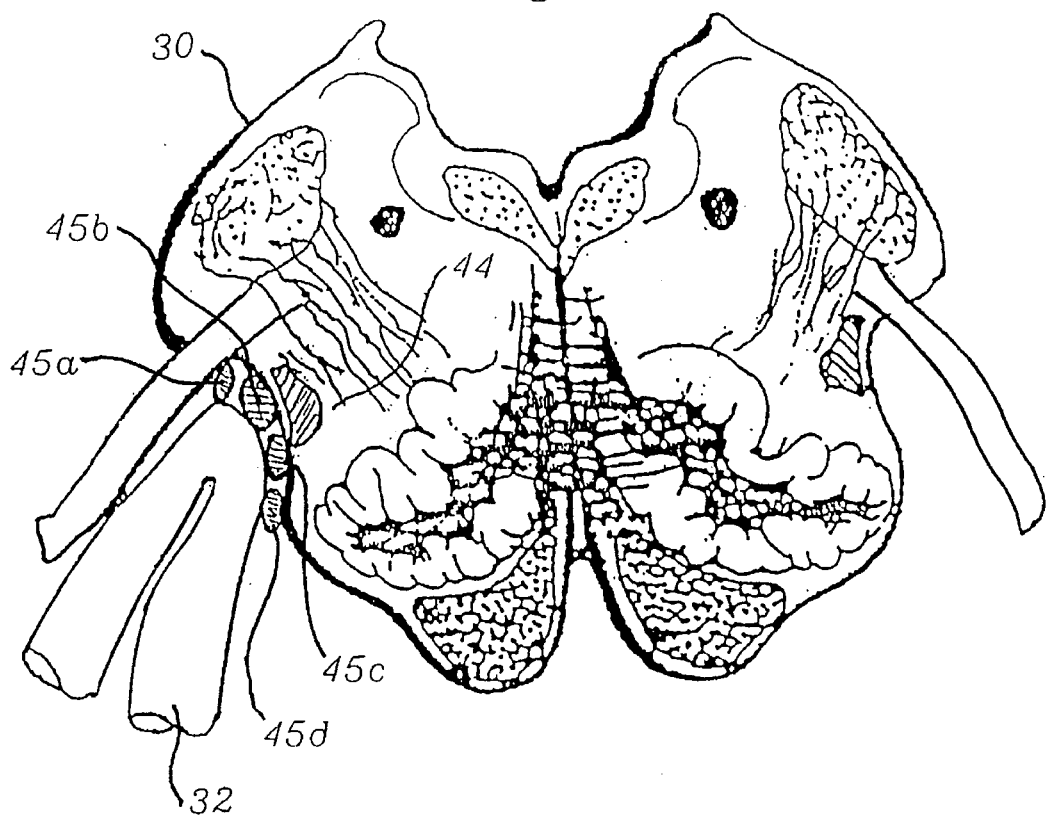
FIG. 3 is a top view of the cross-section in FIG. 2 showing vascular compression of the right ventrolateral medulla.

FIG. 3 illustrates a top view of a cross-section of medulla oblongata 30, in which microvascular decompression was effected. The vertebral artery loop 32 near the root entry zone of the right branch 34 of Cranial X has been lifted away from contact with, and thus decompressing, region 44. To maintain the decompression, at least one neurovascular bridge implant 45a–d is interposed between loop 42 and region 44.

Bridge implants 45a–d, seen in cross-section, can be made of a soft, biocompatible material, for example, a shredded polytetrafluoroethylene (PTFE) felt. Where additional structural support is desirable, implants 45a–d instead can be made of a preconfigured thermoplastic material, that can be formed into a convenient shape for interposition by the surgeon. Thermoplastic implants 45a–d would return to the preconfigured shape over time at the urging of the subject's body temperature. Implants 45a–d can be either PTFE felt, thermoplastic material, or a combination of both types.

Figure 4A:
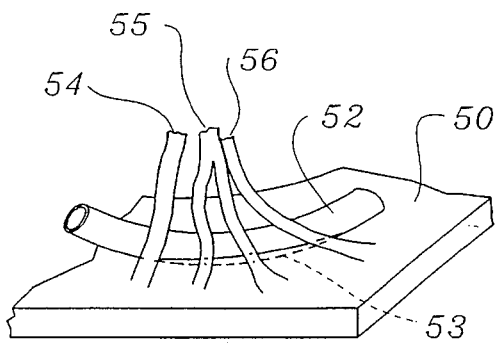
FIGS. 4a–f are illustrations of various vascular configurations with respect the medulla oblongata and adjacent cranial nerves.
Figure 4B:
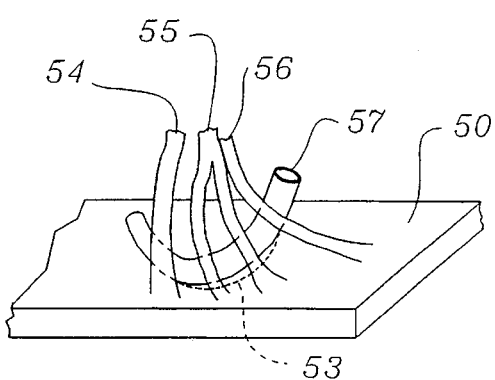
Figure 4C:
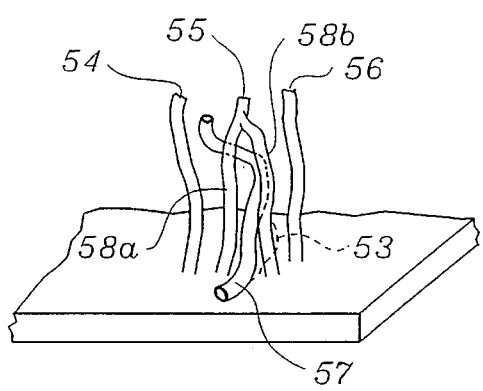
Figure 4D:
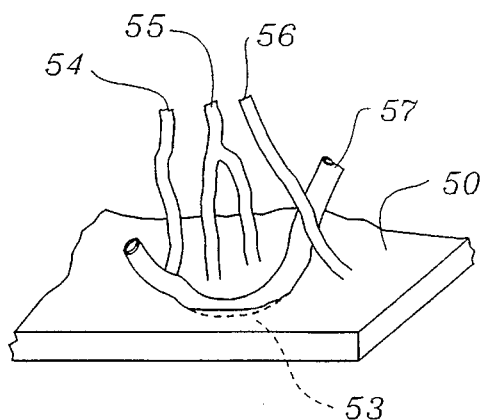
Figure 4E:
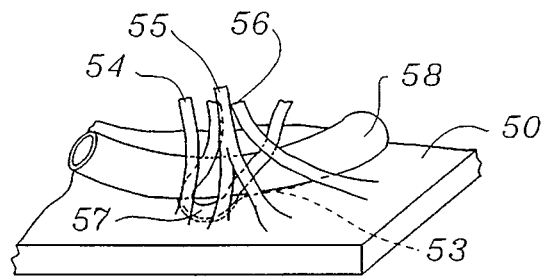
Figure 4F:
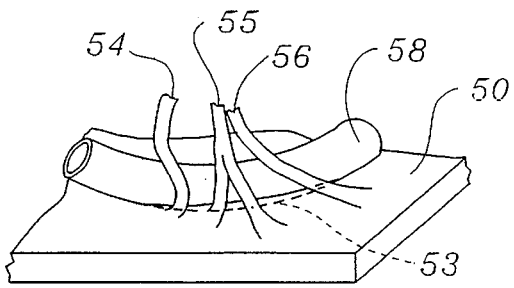

FIGS. 4a–d illustrate some other possible configurations of vascular compression of the medulla and associated cranial nerves. FIG. 4a shows right lateral medulla oblongata 50 being compressed by artery 52 in the vicinity of the root entry zones of Cranial IX 54, Cranial X 55, and the spinal accessory nerve, Cranial XI 56. The pulsatile compression by artery 52 creates a depressed region, or groove, 53 in the right lateral medulla 50. FIG. 4b shows anterior compression of right lateral medulla 50 by PICA 57. In FIG. 4c, PICA 57 is shown coursing between middle fascicles 58a, b of Cranial X 55. FIG. 4d illustrates PICA 57 grooving posteriorly from the cranial direction. FIG. 4e illustrates vertebral artery 58 pushing a loop of PICA 57 into right lateral medulla oblongata 50. FIG. 4f shows dolichoectatic vertebral artery 58 compressing right lateral medulla oblongata 50, to cause groove 50.

Figure 5:
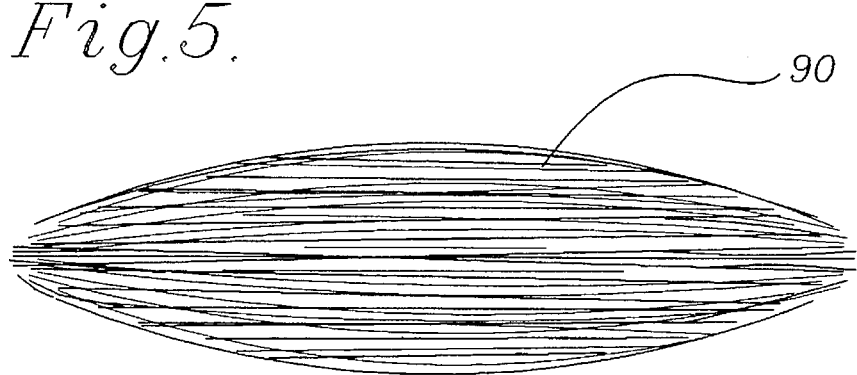
FIG. 5 is a side elevational view of a preconfigured shredded plastic felt neurovascular bridge implant according to the invention herein.

FIG. 5 is an illustration of a soft, biocompatible, shredded-plastic bridge implant 90 which can be composed of multiple fibers, or whiskers, of PTFE, and have a preselected shape. Implant 90 may be, for example, cylinder-, box-, cigar- or wedge-shaped, flattened-ovoid-shaped, and the like. The smallest of implant 90 may consist of a few generally soft and unrolled fibers. Implant 90 can be manufactured with a preselected shape, width, thickness and length, and packaged as a kit along with other PTFE implants having different preselected shapes, widths, thicknesses and lengths. Table 1 describes exemplary lengths, widths, thicknesses, and preselected configurations for certain embodiments of implant 90.

TABLE 1

| SIZE | CIGAR | BOX | WEDGE* |
|---|---|---|---|
| Small | | | |
| Length | 5 mm | 5 mm | 5 mm |
| Width | 2 mm | 2 mm | 2–3 mm |
| Thickness | 2 mm | 1 mm | 2–3 mm |
| Medium | | | |
| Length | 6–8 mm | 6–8 mm | 6–8 mm |
| Width | 2–3 mm | 3 mm | 3–4 mm |
| Thickness | 2–3 mm | 1–2 mm | 3–4 mm |
| Large | | | |
| Length | 7–10 mm | 7–10 mm | 7–10 mm |
| Width | 4 mm | 4 mm | 4–5 mm |
| Thickness | 4 mm | 2 mm | 4–5 mm |
| Extra Large | | | |
| Length | 10–15 mm | 10–15 mm | 10–15 mm |
| Width | 4–5 mm | 5 mm | 5–6 mm |
| Thickness | 4–5 mm | 5 mm | 5–6 mm |

*Wedge width is measured at widest point of the implant. At mid-point, a wedge can be as wide as a cigar-shaped implant of a comparable length.

To enhance the tissue compatibility of the PTFE felt implants, at least a portion of the implant may be coated with silicon. Each of the implants can be protectively packaged to protect against implant fiber compaction, which may tend to cause the in-situ implant to transmit arterial pulsations to the adjacent neural tissue. Also, instead of a pre-cut implant, implant 90 may be derived from a longer, multi-stranded yarn of shredded PTFE of a preselected thickness. In the latter case, the surgeon could tear off the implant material at the preselected length prior to insertion into the subject.

Figure 6A:
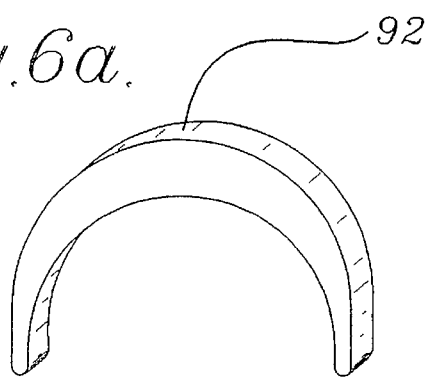
FIG. 6a–c are side elevational views of a thermoplastic neurovascular bridge implant exhibiting shape-memory according to invention herein.
Figure 6B:
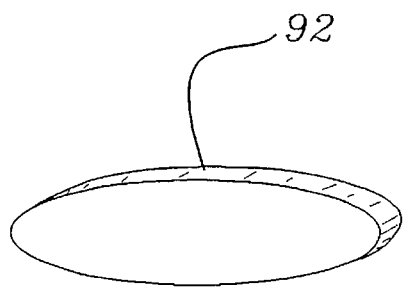
Figure 6C:
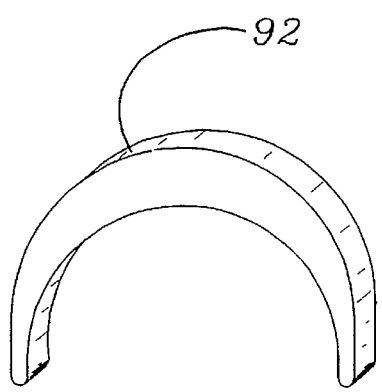

FIGS. 6a–c illustrate the shape-memory function that is inherent in thermoplastic neurovascular bridge implant 92. In FIG. 6a, implant 92 is formed into a preconfigured shape at a first temperature. It is preferred that implant 92 be soft and pliable at room temperature (about 25° C.). During the microvascular compression procedure, the surgeon, or an assistant, can temporarily reform implant 92, FIG. 6b, at a second temperature, such as room temperature, into a shape that is convenient for interposition into the subject's brain between the offending blood vessel(s) and the brainstem. In time, as seen in FIG. 6c, the heat of the subject's body (e.g., about 36° C. to about 37.5° C.) causes implant 92 to return substantially to the preconfigured shape given in FIG. 6a. To facilitate selection and placement, implant 92 can have a color-coded portion, which coding can indicate implant size, final shape, and orientation of the implant curvature. Although implant 92 is shown to be generally arcuate in shape, other preselected configurations also can be used.

One such biocompatible implant material is Shape Memory Polymer (SMP) by Mitsubishi Heavy Industries, Tokyo, Japan. SMP is a "smart" polyurethane-based material that can transform its shape and hardness, and be returned to its original shape. The material can be formed into a "learned" shape at a particular temperature and then cooled, thus forming the shape memory. Implant 92 may be shaped into a configuration by the surgeon that facilitates insertion. When SMP is reheated, implant 92 "remembers" the learned shape. The range of hardness to softness can be customized, and a broad range of transition temperatures can be chosen. Softening can be made to occur at standard glass-transition temperatures of 25° C., 35° C., 45° C., and 55° C. The transition band can be around 8° C. Using SMP, implant 92 can be formed by injection molding, extrusion, coating, casting, and the like.

Figure 7:
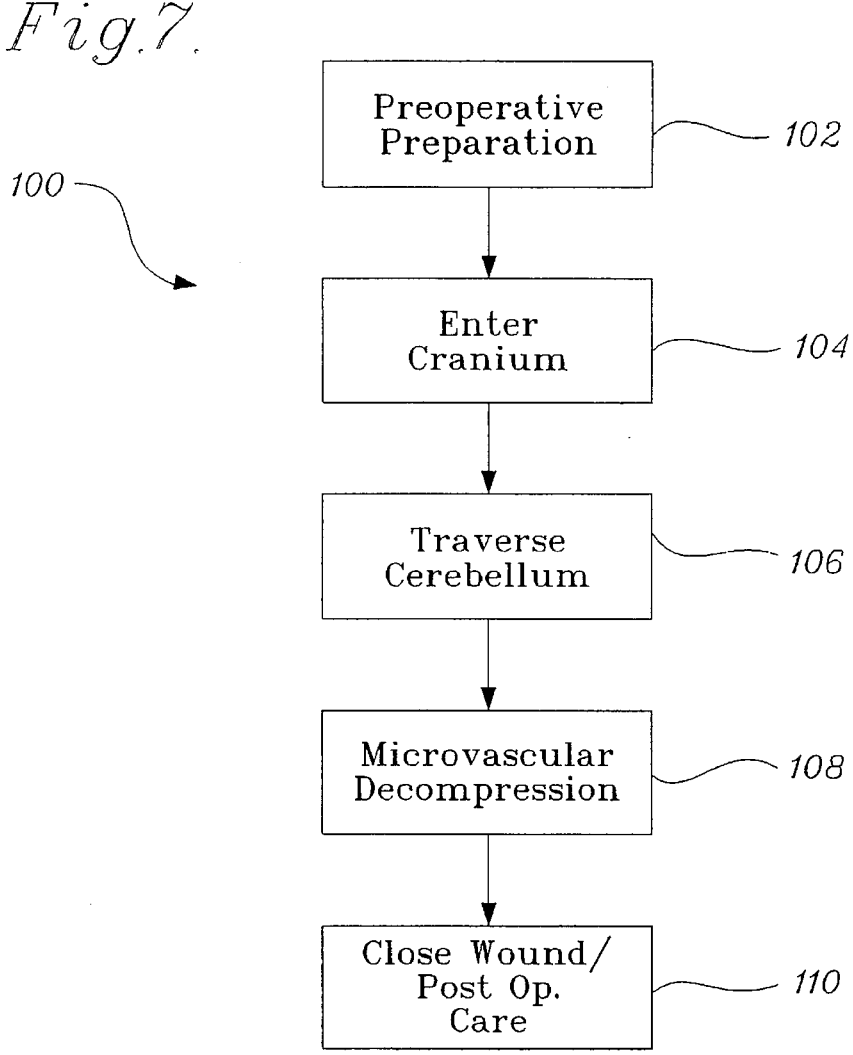
FIG. 7 is a flow diagram of the overall surgical procedure according to the invention herein.
Figure 8:
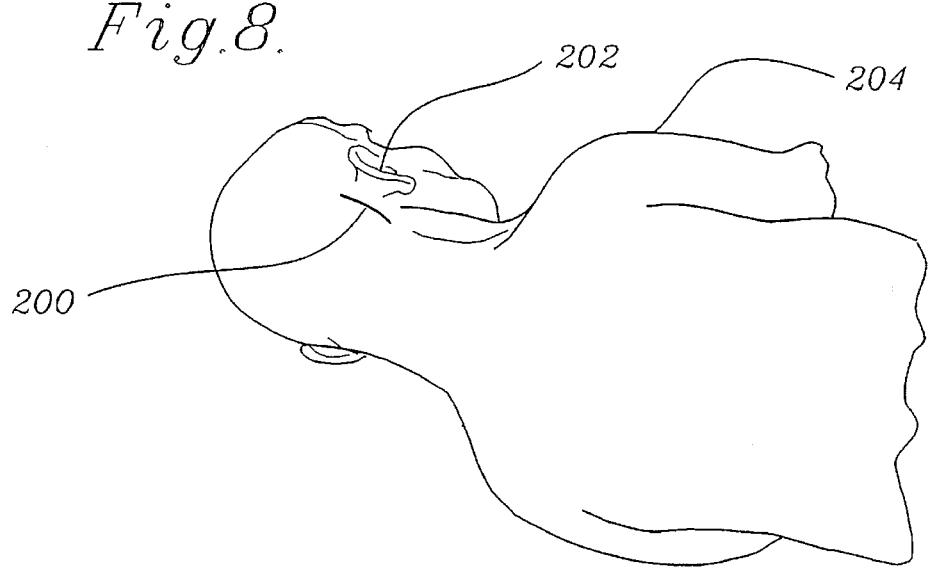
FIG. 8 in an illustration of the top rear view of a surgical subject lying in a left lateral recumbent position.

FIG. 7 describes the overall method 100 according to the invention herein. In general, method 100 includes a preoperative preparation, step 102, of the surgical subject which can include anesthetizing and positioning the subject for convenient access during surgery. For example, in one embodiment of the present invention, the subject can be brought to the operating room, given general anesthesia, and placed in the left lateral decubitus position, as seen in FIG. 8. The subject's head can be immobilized in a 3-point head holder. Furthermore, the subject's neck can be placed on the head holder stretch with the chin slightly flexed, the head rotated slightly to the ipsilataral side and lateral flexion slightly to the contralateral side. The right shoulder can be held out of the way. Continuing in FIG. 7, with the subject thus prepared, the surgeon can enter the cranium, step 104.

In one embodiment of the present invention, it is preferred that a retromastoid craniectomy be performed, although other approaches may be used. A retromastoid incision 200 can be made parallel to and behind the right ear 202 of subject 204 to length of approximately three to six centimeters, as seen in FIG. 8. The length of the incision can be depend upon the configuration, size of build, level of obesity, and degree of musculature of the patient. For certain brachycephalic subjects, a smaller bony opening close to the mastoid process may be indicated, because of the more medial-to-lateral presentation of the cranial nerves in such subjects.

With the opening incision made, hemostasis can be secured in the soft tissues, and a right lateral retromastoid craniectomy can be performed, which goes down to the floor of the occipital plate. The opening into the cranial vault can be approximately 2.5 cm by 3.0 cm. Also, the edge of the exposed cranial bone can waxed to achieve hemostasis, and seal off the bone air cells.

Next, in FIG. 7, the surgeon can transect the meninges and traverse the subject's cerebellum using a preselected pericerebellar procedure, step 106, to gain access to the brainstem. It is important that the surgeon employ a substantial degree of gentleness, restraint, and patience to preserve the exquisitely sensitive cerebellar tissues. It also is important that no artery be torn or perforated. One embodiment of step 106 is described in greater detail in the context of FIG. 9. Once the brainstem and the compressing arteries are exposed, the surgeon can perform microvascular decompression, step 108, of the brainstem and the cranial nerves which affect the target neuroendocrine regulatory system. One embodiment of step 108 is described in the context of FIG. 10.

Once the surgeon has completed the microvascular decompression, step 108, the subject's incision can be closed in an accepted fashion. Prior to closing the incision, gentle irrigation can be performed on the cerebellum using a balanced salt solution, after which the dura mater can be closed in a watertight fashion. Next, the removed cranial bone chips can be replaced or a cranioplasty can be performed, and the exterior incision be closed in a typical way, such as, for example, with sutures. The subject can receive postoperative care, step 110, of the type that is routinely provided to subjects undergoing a posterior fossa operation.

FIG. 9 describes one embodiment of the procedure 120 used to traverse the cerebellum, herein called the pericerebellar procedure, which corresponds to step 106 in FIG. 7. After opening the bone, the dura mater is opened, step 122, low and laterally, and is sewn out of the way. Next, the surgical microscope can be brought into place, and set at medium to high power for the remainder of the intradural part of the operation. A rubber dam and cottonoid can be placed over the cerebellum, also low and laterally. A self-retaining microsurgical retractor with a narrow blade can be used to elevate the cerebellum from the occipital plate, step 124, and then move the cerebellar tissue laterally, without compressing it. Access into the subarachnoid space can be obtained by sharply transecting the arachnoid membrane with a sharp microsurgical instrument or other cutting blade, step 126. Often, a bridging vein can be found over Cranial X which can coagulated and divided, step 128. To verify the effectiveness of the coagulation, the anesthesiologist, under the direction of the surgeon or an assistant, can perform a Valsalva maneuver on the subject.

Next, while gently elevating the cerebellum, step 130, the lower cranial nerves can be identified. When Cranial IX and Cranial X are located, the adjacent cerebellar tissue can be separated therefrom, and the pia-arachnoidal traebeculae, or chordae, can be sharply transected, step 132. The separation of the cerebellar tissues from the cranial nerves is similar to opening a book, in that the cerebellar tissue should be gently lifted, and not compressed. The choroid plexus of the lateral recess of the fourth ventricle can be very vascular but, if it is necessary that it be coagulated, the heat transmitted to Cranial IX and Cranial X should be minimized. Then, the surgeon can expose the right lateral medulla and the root entry zones of Cranial IX and Cranial X, step 134. With the preselected portion of the brain step thus exposed, the surgeon can identify those blood vessels which impinge upon the preselected region.

Frequently, a loop of the vertebral artery, typically the posterior interior cerebellar artery (PICA) and, occasionally, the anterior inferior cerebellar artery (AICA), will be seen compressing and grooving the right lateral medulla in a subject with NIDDM. The aforementioned arteries are part of the vertebral-basilar artery system, and can alone, or in concert with others of this system, compress the surface of the brainstem, and deeply groove it.

The process of microvascular decompression, method 150 in FIG. 10, generally corresponds to step 108 in FIG. 7. Once the surgeon has visualized the offending arteries, step 152, those portions of the blood vessels which are distal to the point of maximum compression are mobilized from the brainstem surface, step 154. As each successive portion is mobilized, a shredded plastic felt neurovascular bridge implant can be interposed between the artery and the brain stem, step 156. The mobilization of the blood vessels and the interposition of the felt implants are repeated, moving in the direction of the point of maximum compression, step 158 until sufficient decompression is achieved. Multiple felt implants may be placed between the blood vessels and the medulla until the blood vessels start to move off of the medulla.

However, in many situations, the offending blood vessels, especially if it is an artery of a large diameter, will continue to distort the medulla even though it is held off of the area of prior compression by the shredded plastic felt implants. In this situation, the surgeon can shape and interpose, step 160, the preconfigured thermoplastic neurovascular bridge implants, which will reconfigure to the predetermined shape, upon exposure to body temperature for a predetermined time period. In general, the convex side of the implant is oriented away from the medulla. When the thermoplastic implant is put into place, it typically becomes loosely anchored by its shape anteriorly, ipsilaterally, and contralaterally, as it reconfigures in accordance with its shape-memory, thus holding the offending artery away from the medulla. In addition, the medulla is supported away from the heat-sensitive implant by the configuration of the implant. Also, additional felt implants may be interposed, step 162, if desired, to provide the desired degree of separation between the offending blood vessels and the brain stem.

While specific embodiments of practicing the invention have been described in detail, it will be appreciated by those skilled in the art that various modifications and alternatives to those details could be developed in light of the overall teachings of the disclosure. Accordingly, the particular arrangements and methods disclosed are meant to be illustrative only and not limiting to the scope of the invention for which is to be given the full breadth of the following claims, and any and all embodiments thereof.

I claim:

1. A method for relieving pressure from a preselected region of the brainstem within the cranium of a subject, the subject having a disorder of the normal neuroendocrine servomechanism, the pressure resulting from the compression of the region by a blood vessel, the method comprising the steps of:

a. gaining access to the preselected region using a first preselected surgical technique;

b. exposing the preselected region according to a second preselected surgical technique;

c. lifting the blood vessel from at least a portion of the region according to a third preselected surgical technique, thereby providing the pressure relief, the neuroendocrine servomechanism being responsive to the pressure relief on the region; and d. inserting a neurovascular bridge implant between the blood vessel and the preselected region, the implant maintaining the pressure relief.

2. The method of claim 1, wherein the first preselected surgical technique is a retromastoid craniectomy.

3. The method of claim 1 wherein the second preselected surgical technique is a pericerebellar procedure.

4. The method of claim 1 wherein the third preselected surgical technique is microvascular decompression.

5. The method of claim 1 wherein the preselected region includes a region of the brainstem selected from the group consisting of a medulla oblongata portion and a tenth cranial nerve portion.

6. The method of claim 1 wherein the blood vessel is an artery and the compression is pulsatile compression.

7. The method of claim 5 wherein the blood vessel is an artery and the compression is pulsatile vascular compression.

8. The method of claim 7 wherein the artery selected from the group consisting of the basilar artery, the vertebral artery, the anterior inferior cerebellar artery, the posterior inferior cerebellar artery, and branches and combinations thereof.

9. The method of claim 5 wherein the medulla oblongata portion includes the right ventrolateral medulla oblongata.

10. The method of claim 1 wherein the pressure relief ameliorates non-insulin-dependent diabetes mellitus.

11. The method of claim 1 wherein the neuroendocrine servomechanism includes the pancreas of the subject and the pressure relief ameliorates non-insulin-dependent diabetes mellitus.

12. The method of claim 4 wherein the compression is pulsatile vascular compression and the blood vessel is selected from the group consisting of the basilar artery, the vertebral artery, the anterior inferior cerebellar artery, the posterior inferior cerebellar artery, and branches and combinations thereof, and the medulla oblongata portion includes the right ventrolateral medulla oblongata.

13. The method of claim 1 wherein the neurovascular bridge implant is one of a preconfigured shredded plastic implant and a preconfigured thermoplastic implant.

14. The method of claim 13 wherein the preconfigured shredded plastic implant is made of polytetrafluoroethylene.

15. The method of claim 13 wherein the preconfigured thermoplastic implant has a shape-memory function, whereby said preconfigured thermoplastic implant returns to a preconfigured shape upon urging of the subject's body temperature to maintain the pressure relief.

16. The method of claim 15 wherein the preconfigured thermoplastic implant is made of a polyurethane-based material having a glass-transition temperature of between about 20° C. and about 60° C. and a transition band of about 8° C.

17. A method for relieving pressure from a preselected region of the brainstem within the cranium of a subject, the subject having a disorder of the normal neuroendocrine servomechanism, the pressure resulting from the compression of the region by a blood vessel, the method comprising the steps of:

a. gaining access to the preselected region using a first preselected surgical technique, the preselected region including the right lateral medulla oblongata;

b. exposing the preselected region according to a second preselected surgical technique;

c. lifting the blood vessel from at least a portion of the region using the microvascular decompression technique, thereby providing the pressure relief, the neuroendocrine servomechanism being responsive to the pressure relief on the region; and d. inserting a neurovascular bridge implant between the blood vessel and the preselected region, the implant maintaining the pressure relief.

18. The method of claim 17, wherein the first preselected surgical technique is a retromastoid craniectomy.

19. The method of claim 17 wherein the second preselected surgical technique is a pericerebellar procedure.

20. The method of claim 17 wherein the blood vessel is an artery and the compression is pulsatile compression, and the artery is selected from the group consisting of the basilar artery, the vertebral artery, the anterior inferior cerebellar artery, the posterior inferior cerebellar artery, and branches and combinations thereof.

21. The method of claim 20 wherein the neuroendocrine servomechanism includes the pancreas of the subject and the pressure relief ameliorates non-insulin-dependent diabetes mellitus.

22. The method of claim 17 wherein the neurovascular bridge implant is one of a preconfigured shredded plastic implant and a preconfigured thermoplastic implant.

23. The method of claim 17 wherein the preconfigured shredded plastic implant is made of polytetrafluoroethylene.

24. The method of claim 17 wherein the preconfigured thermoplastic implant has a shape-memory function, whereby said preconfigured thermoplastic implant returns to a preconfigured shape upon urging of the subject's body temperature to maintain the pressure relief.

25. The method of claim 24 wherein the preconfigured thermoplastic implant is made of a polyurethane-based material having a glass-transition temperature of between about 20° C. and about 60° C. and a transition band of about 8° C.

* * * * *

UNITED STATES PATENT AND TRADEMARK OFFICE
CERTIFICATE OF CORRECTION

PATENT NO. : 5,589,183
DATED : December 31, 1996
INVENTOR(S) : PETER J. JANNETTA It is certified that error appears in the above-indentified patent and that said Letters Patent is hereby corrected as shown below:

On the title page, item
At [56] References Cited, please insert the following references which were omitted:

--J. Neurosurg., Volume 68, "Bilaterial trigeminal neuralgia: a 14 year experience with microvascular decompression," Ian F. Pollack, M.D., et al., April, 1988, pages 559-565--

--J. Neurosurg., Volume 63, "Spasmodic torticollis due to neurovascular compression of the 11th nerve," Carlo A. Pagni et al., November, 1985, pages 789-791--

Signed and Sealed this

Twenty-ninth Day of April, 1997

*Attest:*

BRUCE LEHMAN

*Attesting Officer*     Commissioner of Patents and Trademarks